US012668832B2

(12) United States Patent
Hohng et al.

(10) Patent No.: US 12,668,832 B2
(45) Date of Patent: Jun. 30, 2026

(54) METHOD FOR DETECTING POLYNUCLEOTIDE USING RISC

(71) Applicant: simfliBIO Inc., Seoul (KR)

(72) Inventors: Sungchul Hohng, Seoul (KR); Soochul Shin, Incheon (KR)

(73) Assignee: simfliBIO Inc., Seoul (KR)

( * ) Notice: Subject to any disclaimer, the term of this patent is extended or adjusted under 35 U.S.C. 154(b) by 1036 days.

(21) Appl. No.: 17/421,835

(22) PCT Filed: Aug. 1, 2019

(86) PCT No.: PCT/KR2019/009631
§ 371 (c)(1),
(2) Date: Jul. 9, 2021

(87) PCT Pub. No.: WO2020/204272
PCT Pub. Date: Oct. 8, 2020

(65) Prior Publication Data
US 2022/0098649 A1 Mar. 31, 2022

(30) Foreign Application Priority Data
Apr. 1, 2019 (KR) ........................ 10-2019-0037948

(51) Int. Cl.
| | |
|---|---|
| *C12Q 1/6827* | (2018.01) |
| *C12Q 1/6818* | (2018.01) |
| *C12Q 1/6832* | (2018.01) |
| *C12Q 1/6876* | (2018.01) |

(52) U.S. Cl.
CPC ......... *C12Q 1/6827* (2013.01); *C12Q 1/6832* (2013.01); *C12Q 1/6876* (2013.01); *C12Q 1/6818* (2013.01)

(58) Field of Classification Search
CPC .. C12Q 1/6827; C12Q 1/6818; C12Q 1/6876; C12Q 1/6816; C12Q 1/6832; C12Q 2537/165; C12Q 2563/107; C12Q 2565/601
See application file for complete search history.

(56) References Cited

U.S. PATENT DOCUMENTS

| | | | |
|---|---|---|---|
| 2005/0214818 A1 | 9/2005 | Theurkauf et al. | |
| 2016/0289734 A1* | 10/2016 | Zamore ................ | C12Q 1/6818 |
| 2017/0067050 A1 | 3/2017 | Tuschl et al. | |
| 2021/0164024 A1* | 6/2021 | Feng .................... | C12Q 1/6818 |

FOREIGN PATENT DOCUMENTS

| | | |
|---|---|---|
| KR | 10-2007-0023354 | 2/2007 |
| KR | 20120026927 | 3/2012 |
| KR | 20150128612 | 11/2015 |
| KR | 10-2017-0113336 | 10/2017 |
| KR | 20170138829 | 12/2017 |

OTHER PUBLICATIONS

KIPO, PCT Search Report & Written Opinion of PCT/KR2019/009631 dated Dec. 30, 2019.
Myung Hyun Jo et al., "Single-molecule fluorescence measurements reveal the reaction mechanisms of the core-RISC, composed of human Argonaute 2 and a guide RNA", BMB Rep. 2015; 48(12): 643-644.
Soochul Shin, "Single Molecule FRET Studies on Argonaute protein", Master's Thesis in Science, Department of Biophysics and Chemical Biology, Seoul National University.
Alexander Johnson-Buck et al., "Kinetic fingerprinting to identify and count single nucleic acids", Nature Biotechnology vol. 33, pp. 730-732, Jun. 22, 2015.
Jongjin Lee et al., "Accelerated super-resolution imaging with Fret-Paint", Mol Brain. Dec. 28, 2017;10(1):63. doi: 10.1186/s13041-017-0344-5.
Seung-Ryoung Jung et al., "Dynamic Anchoring of the 3'-End of the Guide Strand Controls the Target Dissociation of Argonaute-Guide Complex", J. Am. Chem. Soc.135, 16865-16871, Oct. 14, 2013.
Myung Hyun Jo et al., "Human Argonaute 2 Has Diverse Reaction Pathways on Target RNAs", Molecular Cell 59, 117-124, Jul. 2, 2015.
Victor Ambros, "microRNAs: Tiny Regulators with Great Potential", Cell, vol. 107, 823-826, Dec. 28, 2001.
Ali M. Ardekani et al., "The Role of MicroRNAs in Human Diseases", Avicenna Journal of Medical Biotechnology, vol. 2, No. 4, Oct.-Dec. 2010.
Yong Sun Lee et al., "MicroRNAs in cancer", Annu Rev Pathol. 2009 ; 4: 199-227. doi:10.1146/annurev.pathol.4.110807.092222.
Heidi Schwarzenbach et al., "Cell-free nucleic acids as biomarkers in cancer patients", Nature Reviews Cancer vol. 11, pp. 426-437, May 12, 2011.
Kai Zhang et al., "Regulation and imaging of gene expression via an RNA interference antagonistic biomimetic probe", Chem. Sci., 8, 4973-4977, May 5, 2017.
Yeh-Hsing Lao et al., "Enhancement of Aptamer Microarray Sensitivity through Spacer Optimization and Avidity Effect", Analytical Chemistry, vol. 81, No. 5, 1747-1754, Mar. 1, 2009.
Xiaolu A. Cambronne et al., "Capturing microRNA targets using an RNA-induced silencing complex (RISC)-trap approach", PNAS, Dec. 11, 2012, 109 (50) 20473-20478; https://doi.org/10.1073/pnas.1218887109.
Soochul Shin et al., "Quantification of purified endogenous miRNAs with high sensitivity and specificity", Nature Communications, vol. 11, Article No. 6033 (2020), Nov. 27, 2020.

* cited by examiner

*Primary Examiner* — Sarae L Bausch
(74) *Attorney, Agent, or Firm* — Sughrue Mion, PLLC

(57) ABSTRACT

Disclosed herein is a method for detecting small RNAs and discriminating single nucleotide polymorphism at a single molecule level, and specifically to a method for detection of small RNAs, whereby the detection and quantitation of small RNAs and the identification of single nucleotide polymorphism (SNP) can be achieved.

13 Claims, 10 Drawing Sheets

Specification includes a Sequence Listing.

【Fig.1a】
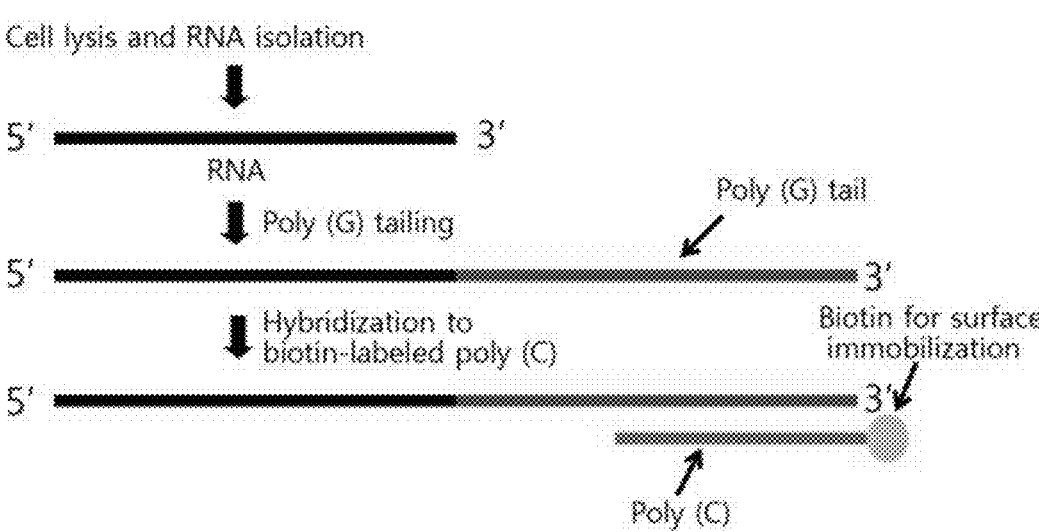

【Fig.2a】
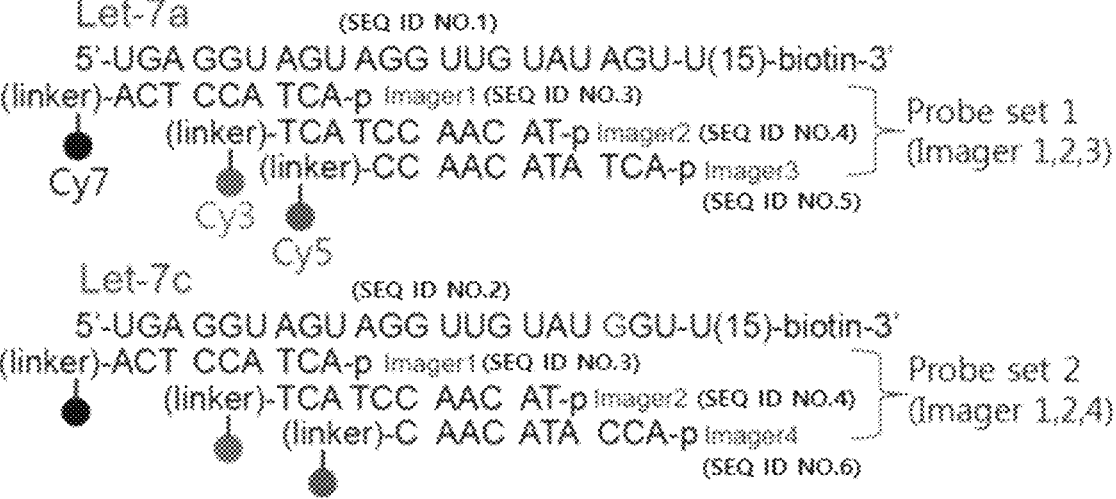
【Fig.2b】
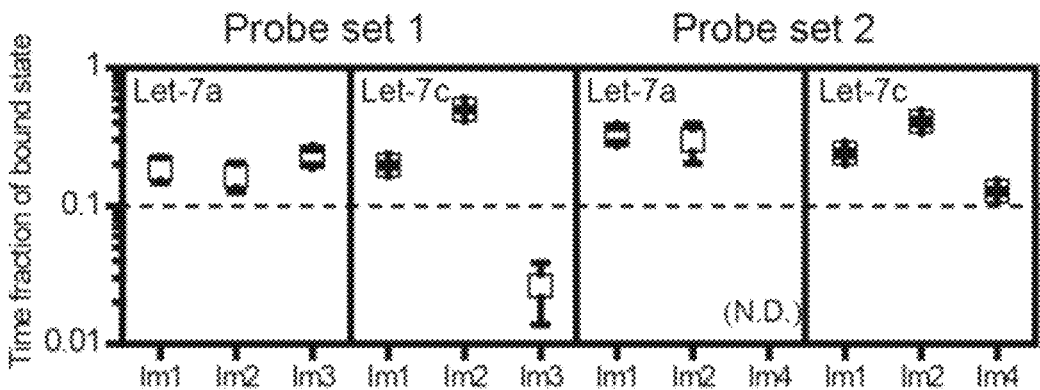

[Fig.2c]
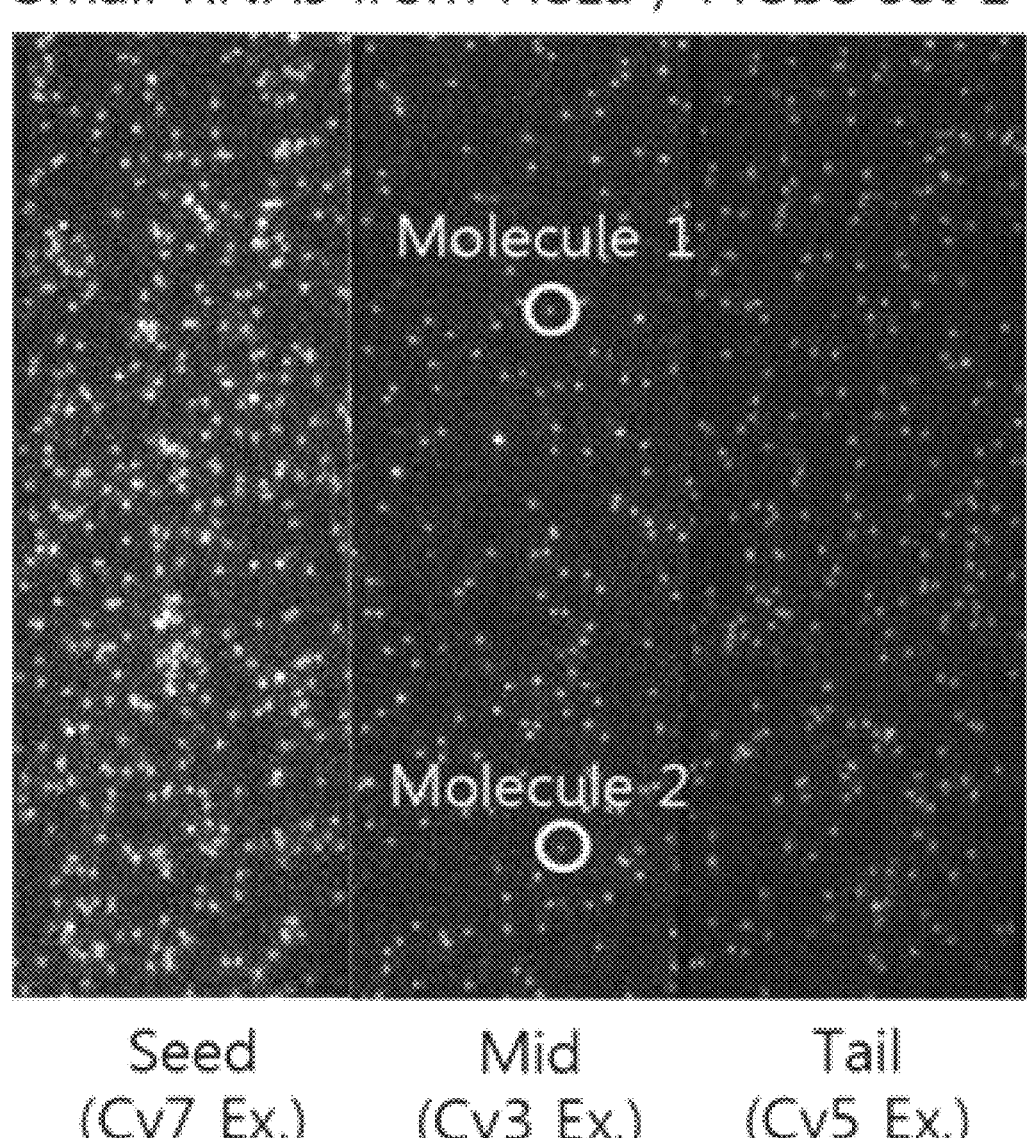
Small RNAs from HeLa / Probe set 1

[Fig.4a]

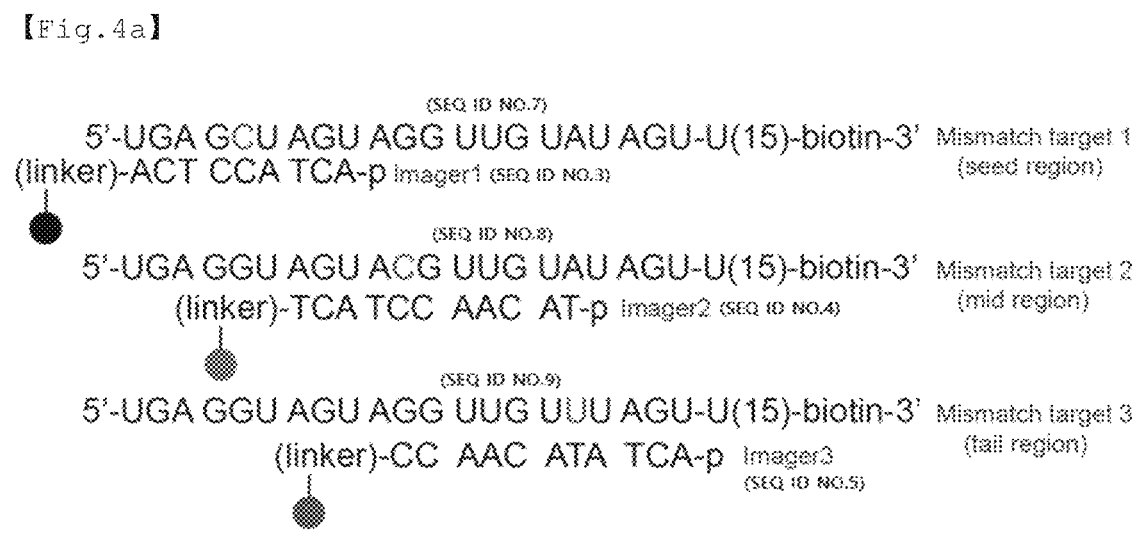

(SEQ ID NO.7)

5'-UGA GCU AGU AGG UUG UAU AGU-U(15)-biotin-3'    Mismatch target 1

(linker)-ACT CCA TCA-p Imager1 (SEQ ID NO.3)    (seed region)

(SEQ ID NO.8)

5'-UGA GGU AGU ACG UUG UAU AGU-U(15)-biotin-3'    Mismatch target 2

(linker)-TCA TCC AAC AT-p Imager2 (SEQ ID NO.4)    (mid region)

(SEQ ID NO.9)

5'-UGA GGU AGU AGG UUG UUU AGU-U(15)-biotin-3'    Mismatch target 3

(linker)-CC AAC ATA TCA-p Imager3    (tail region)

(SEQ ID NO.5)

【Fig.4c】
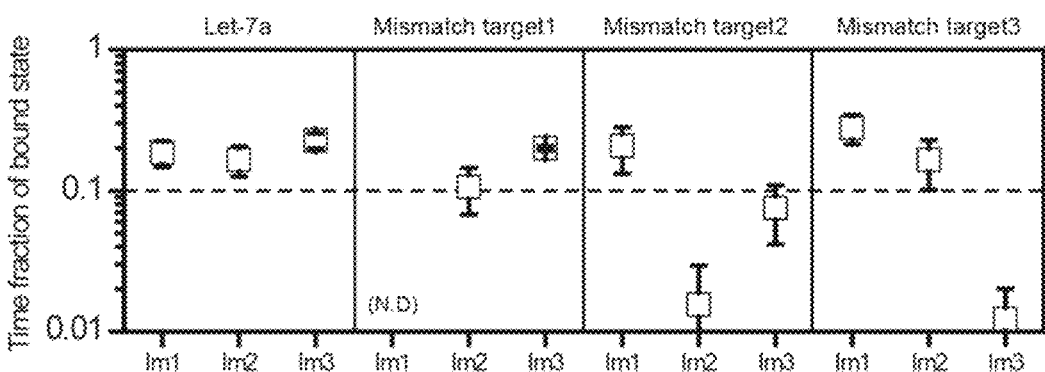

SEQUENCE LISTING

<160> NUMBER OF SEQ ID NOS: 9

<210> SEQ ID NO 1
<211> LENGTH: 21
<212> TYPE: RNA
<213> ORGANISM: Artificial Sequence
<220> FEATURE:
<223> OTHER INFORMATION: (synthetic) let-7a miRNA

<400> SEQUENCE: 1
ugagguagua gguuguauag u                                                              21

<210> SEQ ID NO 2
<211> LENGTH: 21
<212> TYPE: RNA
<213> ORGANISM: Artificial Sequence
<220> FEATURE:
<223> OTHER INFORMATION: (synthetic) let-7c miRNA

<400> SEQUENCE: 2
ugagguagua gguuguaugg u                                                              21

<210> SEQ ID NO 3
<211> LENGTH: 21
<212> TYPE: DNA
<213> ORGANISM: Artificial Sequence
<220> FEATURE:
<223> OTHER INFORMATION: (synthetic) Imager 1

<400> SEQUENCE: 3
actacctcat tttttttttt t                                                              21

<210> SEQ ID NO 4
<211> LENGTH: 21
<212> TYPE: DNA
<213> ORGANISM: Artificial Sequence
<220> FEATURE:
<223> OTHER INFORMATION: (synthetic) Imager 2

<400> SEQUENCE: 4
tacaacctac tcattttttt t                                                              21

<210> SEQ ID NO 5
<211> LENGTH: 21
<212> TYPE: DNA
<213> ORGANISM: Artificial Sequence
<220> FEATURE:
<223> OTHER INFORMATION: (synthetic) Imager 3

<400> SEQUENCE: 5
actatacaac cattatttat t                                                              21

<210> SEQ ID NO 6
<211> LENGTH: 21
<212> TYPE: DNA
<213> ORGANISM: Artificial Sequence
<220> FEATURE:
<223> OTHER INFORMATION: (synthetic) Imager 4

<400> SEQUENCE: 6
accatacaac ttttatttat t                                                              21

<210> SEQ ID NO 7
<211> LENGTH: 21
<212> TYPE: RNA
<213> ORGANISM: Artificial Sequence -continued

```
<220> FEATURE:
<223> OTHER INFORMATION: (synthetic) Mismatch target 1 (seed region)

<400> SEQUENCE: 7
ugagcuagua gguuguauag u                                                21

<210> SEQ ID NO 8
<211> LENGTH: 21
<212> TYPE: RNA
<213> ORGANISM: Artificial Sequence
<220> FEATURE:
<223> OTHER INFORMATION: (synthetic) Mismatch target 2 (mid region)

<400> SEQUENCE: 8
ugagguagua cguuguauag u                                                21

<210> SEQ ID NO 9
<211> LENGTH: 21
<212> TYPE: RNA
<213> ORGANISM: Artificial Sequence
<220> FEATURE:
<223> OTHER INFORMATION: (synthetic) Mismatch target 3 (tail region)

<400> SEQUENCE: 9
ugagguagua gguuguuuag u                                                21
```

METHOD FOR DETECTING POLYNUCLEOTIDE USING RISC

TECHNICAL FIELD

The present disclosure relates to a method for detecting small RNAs at a single molecule level, using an RNA-induced silencing complex (RISC), which is a probe-Argonaute enzyme complex, and total internal reflection fluorescence microscopy (TIRF), whereby the detection and quantitation of small RNAs, especially miRNA and the identification of single nucleotide polymorphism (SNP) can be achieved.

BACKGROUND ART

A microRNA (miRNA) is a short (~22 nt) non-coding RNA that functions to regulate gene expression through post-transcriptional gene silencing. The expression of miR-NAs must be stringently regulated, and the dysregulation of miRNAs is associated with cellular malfunction and numerous diseases. Thus, precise profiling of miRNA expression is becoming very important in both the biology and medical fields. Reports have revealed that numerous miRNAs are poorly controlled in a disease-specific manner in a broad spectrum of cancers, demonstrating that many miRNAs play an important role in cancer development. Currently, miR-NAs are emerging as promising diagnostic biomarkers. Stable and diagnostically useful miRNAs have been detected in the blood and are considered ideal tumor markers for early detection of cancer.

However, miRNAs are currently difficult to detect due to the small sizes (~22 nt) thereof and the high homology of miRNA family members which are different by only about one single base. It is the weakness of the standard analysis method based on PCR amplification. Accordingly, it is necessary to develop a technology for detecting miRNAs with high specificity and sensitivity.

The Argonaute protein family plays a central role in RNA silencing processes. Argonaute proteins bind different classes of small non-coding RNAs, comprising microRNAs (miRNAs), small interfering RNAs (siRNAs), and Piwi-interacting RNAs (piRNAs), and induce mRNA cleavage or translation inhibition by attracting small RNAs and guiding them to their specific targets having a complementary sequence.

A total internal reflection fluorescence microscope (TIRF) is a type of apparatus which can observe fluorescent material in the region of 200 nm or less called evanescence field, and can realize changes in single molecule units with high resolution images. TIRF does not acquire a whole image of a fluorescent sample, but an image of the sample only at interface (evanescence field) by using the total reflection of laser (light refracted at an interface of a sample) and thus can acquire accurate images of an interface by excluding interference to fluorescent light.

So far, there has not been such a case of applying the Argonaute protein as a probe-binding enhancer to single molecule detection technology, and nothing is known about novel single molecule detection technology using TRIF capable of quantifying miRNAs without amplification.

DISCLOSURE

Technical Problem

An aspect of the present disclosure provides a protein-nucleic acid complex in which an Argonaute protein is associated with a nucleic acid molecule having a nucleic acid sequence complementary to a target nucleic acid region in a polynucleotide to be detected.

Another aspect of the present disclosure provides a polynucleotide detecting composition comprising a protein-nucleic acid complex in which an Argonaute protein is associated with a nucleic acid molecule, wherein the nucleic acid molecule has a nucleic acid sequence complementary to a target nucleic acid region in a polynucleotide to be detected, and the nucleic acid molecule is conjugated with a fluorophore.

Another aspect of the present disclosure provides a polynucleotide detecting method comprising a step of contacting the polynucleotide-detecting composition with a biological sample.

Another aspect of the present disclosure provides a method for detecting a single nucleotide polymorphism (SNP), the method comprising 1) a step of contacting the polynucleotide detecting composition with a biological sample comprising a polynucleotide to be detected or with a plate onto which the biological sample is immobilized.

In an embodiment, the polynucleotide detecting method or the single nucleotide polymorphism detecting method may further comprise 2) a step of two or more different fluorescent signals resulting from the contact after the contacting step. In another embodiment, the polynucleotide detecting method or the single nucleotide polymorphism detecting method may further comprise 3) a step of calculating a time of bound state (duty cycle) for each of the two or more different fluorescent signals after the measuring step. In another embodiment, the polynucleotide detecting method or the single nucleotide polymorphism detecting method may further comprises 4) a step of determining that the biological sample comprises the polynucleotide to be detected when each of the calculated time fractions of bound state is a threshold or higher after the calculating step. In one embodiment, the polynucleotide to be detected may be composed of a single polynucleotide or two or more different polynucleotides. When the polynucleotide to be detected is composed of two or more different polynucleotides, they may be subjected simultaneously or sequentially to the step 1), steps 1) and 2), steps 1, 2), and 3), or steps 1), 2) 3) and 4).

Technical Solution

Leading to the present disclosure, intensive and thorough research resulted in the finding that a protein-nucleic acid complex in which an Argonaute protein and a nucleic acid molecule are associated with each other can increase a binding rate between the nucleic acid molecule and a polynucleotide to be detected and that two or more different protein-nucleic acid complexes, when conjugated with respective fluorophores, can be used to detect the polynucleotide to be detected only by measuring fluorescent signals without separate amplification, whereby single nucleotide polymorphism (SNP) can be analyzed.

The present disclosure provides a protein-nucleic acid complex in which an Argonaute protein and a nucleic acid molecule are associated with each other, a polynucleotide detecting composition, and a polynucleotide detecting method using same. Taking advantage of a fluoro-imaging technique, the polynucleotide detecting method of the present disclosure can scan the entire region of a polynucleotide without using a locked nucleic acid (LNA) complementary to the polynucleotide to be detected. In addition, polynucleotide detecting method of the present disclosure enjoys the advantage of being faster in detecting rate by up to 10 folds due to the use of the Argonaute protein.

In addition, the detecting method of the present disclosure is verified to be a single-molecule detection method that is very specific and sensitive for a polynucleotide to be detected and can accurately detect a subject of interest in spite of a difference by only one base.

An aspect of the present disclosure pertains to a protein-nucleic acid complex in which an Argonaute protein is associated with a nucleic acid molecule having a nucleic acid sequence complementary to a target nucleic acid region in a polynucleotide to be detected.

The nucleic acid molecule may be a fluorophore-conjugated molecule.

The nucleic acid molecule may comprise a linker. The linker may bear an amine group. In this regard, the fluorophore may be conjugated to the nucleic acid molecule via the amine group of the linker.

The polynucleotide to be detected may be at least one selected from the group consisting of DNA, RNA, and miRNA.

The nucleic acid molecule may consist of 5 to 50 nucleotides.

The nucleic acid molecule may be DNA or RNA.

Another aspect of the present disclosure pertains to a polynucleotide detecting composition comprising a protein-nucleic acid complex in which an Argonaute protein and a nucleic acid molecule are associated with each other, wherein the nucleic acid molecule comprises a nucleic acid sequence complementary to a target nucleic acid region in a polynucleotide to be detected and is conjugated with a fluorophore.

The target nucleic acid region comprises 5 to 15 consecutive nucleotides in the polynucleotide to be detected.

The composition may comprise two or more different protein-nucleic acid complexes wherein the two or more different protein-nucleic acid complexes comprise nucleic acid sequences complementary to two or more different target nucleic regions in the polynucleotide to be detected.

The two or more different protein-nucleic acid complexes may be conjugated with two or more different fluorophores that generate respective signals.

The nucleic acid molecule may comprise a linker which bears an amine group and the fluorophores may be conjugated to the nucleic acid molecule via the linker.

A further aspect of the present invention is concerned with a polynucleotide detecting method comprising a step of contacting the polynucleotide-detecting composition with a biological sample.

The polynucleotide may be at least one selected from the group consisting of DNA, RNA, and miRNA.

The biological sample may be an isolated cell, a cytolysate, a cell extract, a cell lysate, or an isolated DNA or RNA.

Contemplated according to another embodiment of the present disclosure is a polynucleotide detecting method comprising the steps of: contacting the polynucleotide detecting composition with a biological sample; measuring a fluorescent signal resulting from the contact; and calculating a time fraction of bound state from the measured fluorescent signal.

The polynucleotide detecting method may further comprise a step of determining that the biological sample comprises the polynucleotide to be detected when the calculated time fraction of bound state is a threshold or higher.

The polynucleotide detecting method may be carried out in at least two rounds using different nucleic acid complexes, the nucleic acid complexes comprising respective nucleotide sequences complementary to different target nucleic acid regions in the polynucleotide to be detected.

The polynucleotide detecting method may further comprise a step of determining that the biological sample comprises the polynucleotide to be detected when all of the calculated time fractions of bound state in the individual rounds are a threshold or higher. In this case, the protein-nucleic acid complexes different from each other have nucleotide sequences respectively complementary to different target nucleic acid regions in the polynucleotide to be detected, and may be labeled with the same fluorophore. That is, the different protein-nucleic acid complexes may be labeled with the same fluorophore, but may have nucleotide sequences respectively complementary to different target nucleic acid regions in a polynucleotide to be detected. In this regard, the polynucleotide detecting method may further comprise a step in which the method is repeatedly conducted while the different protein-nucleic acid complexes are used sequentially one by one, a time fraction of bound state for each complex is calculated, and when all of the calculated time fractions of bound state are a threshold or higher, the biological sample is determined to comprise the polynucleotide to be detected. Therefore, the different protein-nucleic acid complexes may be labeled with different fluorophores, but the same fluorophore may be used to label the different complexes. When the different complexes are labeled with the same fluorophore, the polynucleotide detecting method may be repetitively conducted to calculate time fractions of bound state.

Another embodiment of the present disclosure pertains to a polynucleotide detecting method, comprising the steps of: contacting the polynucleotide detecting composition with a biological sample; measuring two or more different fluorescent signals resulting from the contact; and calculating respective time fractions of bound state from the two or more different fluorescent signals measured.

The polynucleotide detecting method may further comprise a step of determining that the biological sample comprises the polynucleotide to be detected when all of the calculated time fractions of bound state is a threshold or higher.

The biological sample may contain a polynucleotide having a nucleotide sequence homology of 90% or higher, 91% or higher, 92% or higher, 93% or higher, 94% or higher, 95% or higher, 96% or higher, 97% or higher, 98% or higher, 99% or higher (upper limit is 100%) to the polynucleotide to be detected.

The step of measuring fluorescent signals may be conducted using at least one selected from the group consisting of total internal reflection fluorescence microscopy (TIRF), confocal microscopy, Epi-fluorescence microscopy, HiLo microscopy, and line-scanning confocal microscopy.

Another embodiment of the present disclosure pertains to a method for detecting single nucleotide polymorphism (SNP), the method comprising a step of contacting the polynucleotide detecting composition with a biological sample containing a polynucleotide to be detected.

Below, a detailed description will be given of the present disclosure.

The term "detecting method" as used in conjugation with "at a single molecule level" herein refers to a method for detecting a signal from one actual monomer, but not from a collection of molecules in ensemble or bulk.

An aspect of the present invention provides a protein-nucleic acid complex in which an Argonaute protein and a nucleic acid molecule are associated with each other. For example, the protein-nucleic acid complex may be RISC (RNA-induced silencing complex). Alternatively, the protein-nucleic acid complex may be core-RISC. Meant by the core-RISC is a complex comprising an Argonaute protein and a guide strand, without an additional factor.

The "Argonaute protein" may be derived from Argonautes found in various organisms comprising eukaryotes, prokaryotes, Archaea, etc. The origin of the Argonaute protein may be versatile from bacteria to animals, plants, human, and so on without limitations. By way of example, the Argonaute protein may be derived from at least one selected from the group consisting of hAgo2 (from Human) Q9UKV8, TtAgo (from *Thermus thermophiles*) Q746M7, PfAgo (from *Pyrococcus furiosus*) Q8U3D2, and CbAgo (from *Clostridium butyricum*).

As used herein, the term "nucleic acid molecule" may refer to DNA or RNA and to, for example, DNA. Meant by the term "nucleic acid molecule" is a DNA probe or an RNA probe, which may comprise a nucleic acid sequence complementary to a target nucleic acid in a polynucleotide to be detected.

The nucleic acid molecule may additionally comprise a linker at either or both of the 5'- and the 3'-terminal of the probe region of the nucleic acid sequence complementary to the target nucleic acid region, for example, at the 3'-terminal.

The nucleic acid molecule may comprise or be composed of 5 to 50, 5 to 45, 5 to 40, 5 to 35, 5 to 30, 5 to 29, 5 to 28, 5 to 27, 5 to 26, 8 to 50, 8 to 45, 8 to 40, 8 to 35, 8 to 30, 8 to 29, 8 to 28, 8 to 27, 8 to 26, 10 to 50, 10 to 45, 10 to 40, 10 to 35, 10 to 30, 10 to 29, 10 to 28, 10 to 27, 10 to 26, 12 to 50, 12 to 45, 12 to 40, 12 to 35, 12 to 30, 12 to 29, 12 to 28, 12 to 27, 12 to 26, 15 to 50, 15 to 45, 15 to 40, 15 to 35, 15 to 30, 15 to 29, 15 to 28, 15 to 27, 15 to 26, 16 to 50, 16 to 45, 16 to 40, 16 to 35, 16 to 30, 16 to 29, 16 to 28, 16 to 27, 16 to 26, 18 to 50, 18 to 45, 18 to 40, 18 to 35, 18 to 30, 18 to 29, 18 to 28, 18 to 27, 18 to 26, 5 to 15, 5 to 13, 5 to 11, 7 to 15, 7 to 13, 7 to 11, 9 to 15, 9 to 13, or 9 to 11 nucleotides, for example, 18 to 26 nucleotides. The nucleic acid molecule may comprise a linker designed to be labeled with a fluorophore.

In the nucleic acid molecule, the probe region complementary to a target nucleic acid region may comprise 5 to 13, 5 to 11, 7 to 15, 7 to 13, 7 to 11, 9 to 15, 9 to 13, or 9 to 11 nucleotides, but without limitations thereto. The length of the probe region may be properly controlled to cover the overall region or a desired specific region of the polynucleotide to be detected in consideration of the length of the polynucleotide and/or the length of target nucleic acid region.

The "linker" may be formed at the end of the nucleic acid in the protein-nucleic acid complex such that the nucleic acid contains nucleotides long enough to easily ensure loading to the protein. Alternatively, the "linker" may be formed at the end of the nucleic acid to link the nucleic acid to a fluorophore. The "linker" may be formed at the end of the nucleic acid in order to achieve both the ease of linking the nucleic acid to the protein and the linkage between the nucleic acid and a fluorophore. In detail, the nucleic acid molecule may comprise at the 3' end thereof a linker consisting of or containing 4 to 15 nucleotides, for example, 4 to 14, 4 to 13, 4 to 12, 4 to 9, 4 to 8, 5 to 8, 5 to 7, 6 to 15, 6 to 14, 6 to 13, 6 to 12, 8 to 15, 8 to 14, 8 to 13, 8 to 12, 9 to 15, 9 to 14, 9 to 13, 9 to 12, 10 to 15, 10 to 14, 10 to 13, or 10 to 12 nucleotides. However, the length of the linker is properly set such that the nucleic acid molecule has 5 to 30 nucleotides and preferably 18 to 26 nucleotides in total, but without limitations thereto. The linker may be composed of any nucleotide and, for example, may be any one of the underlined polynucleotides of SEQ ID NOS: 3 to 6 in Table 1.

The linker comprises a moiety to which a fluorescent for labeling the nucleic acid molecule can be conjugated. For example, the linker may comprise a nucleotide having an amine ($NH_2$) group-bearing carbon chain attached thereto, e.g., iAmMC6T (Int Amino Modifier C6 dT). The fluorophore is coupled to the amine group of the linker and can label the nucleic acid molecule.

According to an embodiment, the nucleic acid molecule may comprise two or more different molecules, for example, 2 to 10, 2 to 9, 2 to 8, 2 to 7, 2 to 6, 2 to 4, 2 to 3, 3 to 10, 3 to 9, 3 to 9, 3 to 7, 3 to 6, 3 to 5, or 3 to 4 different molecules, and preferably three or more different molecules. The two or more different nucleic acid molecules may be in part (e.g., 1 to 5 nucleotides) overlapped with each other, or may cover a part or entirety of the polynucleotide to be detected.

The nucleic acid molecule may be DNA or RNA, for example, DNA.

The nucleic acid molecule may be labeled and conjugated with a fluorophore. Two or different nucleic acid molecules may be conjugated with substances generating respective different signals.

The target nucleic acid region may comprise 5 to 15 nucleotides, for example, 5 to 13, 5 to 11, 7 to 15, 7 to 13, 7 to 11, 9 to 15, 9 to 13, or 9 to 11 nucleotides.

The nucleic acid molecule contained in the polynucleotide-detecting composition is conjugated and labeled with a fluorescent or a quantum dot. The two or more different nucleic acid molecules may be conjugated with substances that generate respective different signals.

So long as it has a high quantum yield sufficiently to make single molecule detection, any fluorophore can be used as the fluorophore that can be used for labeling the nucleic acid molecule, without limitations. For example, the fluorophore may be at least one selected from the group consisting of Alexa Fluor 405, Alexa Fluor 488, Cy3, Cy3.5, Cy5, Cy5.5-Allophycocyanin, Cy7, and Alexa Fluor 790.

An aspect of the present disclosure provides a method for detection of a polynucleotide, the method comprising a step of contacting the polynucleotide-detecting composition with a biological sample.

The detection method may comprise a step of extracting a biological sample from a subject prior to the step of contacting the polynucleotide-detecting composition with a biological sample.

The biological sample may be an isolated cell, a cytolysate, a cell extract, a cell lysate, or an isolated DNA or RNA. So long as it is an RNA, any type RNA, for example, miRNA may be used as the polynucleotide to be detected, without limitations.

The biological sample may comprise a polynucleotide to be detected. The polynucleotide to be detected may contain or be composed of 10 to 500, 10 to 400, 10 to 300, 10 to 200, 10 to 150, 10 to 100, 10 to 90, 10 to 80, 10 to 70, 10 to 60, or 10 to 50 nucleotides, but is not limited thereto. In addition, a greater number of nucleotides may be allowed for the polynucleotide because only a desired region can also be detected. The polynucleotide to be detected may be two or more, for example, two, three, four, five, six, seven, eight, nine, or ten different polynucleotides. For the purpose of binding to a reaction chamber (substrate) surface, the polynucleotide to be detected may be modified at 5' and/or 3' terminus thereof with poly-G tailing, poly-A tailing, poly-U/T tailing, or poly-C tailing. According to the modification types, biotin poly U, biotin poly A, or biotin poly G may be used instead of biotin poly C.

The biological sample may contain a polynucleotide similar in sequence homology to the polynucleotide to be detected. According to an embodiment of the present disclosure, even when the biological sample does not contain the polynucleotide to be detected, but only contains a polynucleotide which is one base different from the polynucleotide to be detected, accurate decision can be made with respect to the fact that the biological sample does not contain the polynucleotide to be detected.

The polynucleotide that is similar in sequence homology to the polynucleotide to be detected may have a sequence homology of 10% (inclusive) to 100% (exclusive), 15% (inclusive) to 100% (exclusive), 20% (inclusive) to 100% (exclusive), 25% (inclusive) to 100% (exclusive), 30% (inclusive) to 100% (exclusive), 35% (inclusive) to 100% (exclusive), 40% (inclusive) to 100% (exclusive), 45% (inclusive) to 100% (exclusive), 50% (inclusive) to 100% (exclusive), 55% (inclusive) to 100% (exclusive), 60% (inclusive) to 100% (exclusive), 65% (inclusive) to 100% (exclusive), 70% (inclusive) to 100% (exclusive), 75% (inclusive) to 100% (exclusive), 80% (inclusive) to 100% (exclusive), 85% (inclusive) to 100% (exclusive), 90% (inclusive) to 100% (exclusive), 91% (inclusive) to 100% (exclusive), 92% (inclusive) to 100% (exclusive), 93% (inclusive) to 100% (exclusive), 94% (inclusive) to 100% (exclusive), 95% (inclusive) to 100% (exclusive), 96% (inclusive) to 100% (exclusive), 97% (inclusive) to 100% (exclusive), 98% (inclusive) to 100% (exclusive), or 99% (inclusive) to 100% (exclusive) to the polynucleotide to be detected.

Alternatively, the polynucleotide that is similar in sequence homology to the polynucleotide to be detected may be different by 1 to 30 nucleotides (both inclusive), 1 to 29 nucleotides (both inclusive), 1 to 28 nucleotides (both inclusive), 1 to 27 nucleotides (both inclusive), 1 to 26 nucleotides (both inclusive), 1 to 25 nucleotides (both inclusive), 1 to 24 nucleotides (both inclusive), 1 to 23 nucleotides (both inclusive), 1 to 22 nucleotides (both inclusive), 1 to 21 nucleotides (both inclusive), 1 to 20 nucleotides (both inclusive), 1 to 19 nucleotides (both inclusive), 1 to 18 v (both inclusive), 1 to 17 nucleotides (both inclusive), 1 to 16 nucleotides (both inclusive), 1 to 15 nucleotides (both inclusive), 1 to 14 nucleotides (both inclusive), 1 to 13 nucleotides (both inclusive), 1 to 12 nucleotides (both inclusive), 1 to 11 nucleotides (both inclusive), 1 to 10 nucleotides (both inclusive), 1 to 9 nucleotides (both inclusive), 1 to 8 nucleotides (both inclusive), 1 to 7 nucleotides (both inclusive), 1 to 6 nucleotides (both inclusive), 1 to 5 nucleotides (both inclusive), 1 to 4 nucleotides (both inclusive), 1 to 3 nucleotides (both inclusive), 1 to nucleotides 2 (both inclusive), or 1 nucleotide from the polynucleotide to be detected. According to a particular embodiment of the present disclosure, even when different by only one nucleotide from the polynucleotide to be detected, a polynucleotide can be accurately discriminated from the polynucleotide to be detected.

According to an embodiment of the present disclosure, the step of contacting the polynucleotide-detecting composition may be conducted on a detection chip comprising a fixing polynucleotide comprising a quartz slide coated with a biotin-conjugated polymer, streptavidin, and nucleotides conjugated with biotin, and total polynucleotides extracted from a sample. In addition, the total polynucleotides may be tailed at the 3' terminus thereof with a polynucleotide which is tens of bases long and complementary to the fixing polynucleotide. The polynucleotide extracted from a sample is immobilized to the detection chip due to the binding affinity for the complementary fixing polynucleotide.

The polynucleotide-detecting composition may comprise two or more Argonaute protein-nucleic acid complexes in which Argonaute proteins and nucleic acid molecules are associated with each other and, for example, three Argonaute protein-nucleic acid complexes conjugated with fluorescents generating respective different signals.

According to an embodiment, three protein-nucleic acid complexes, when used, may comprise nucleic acid sequences complementary to seed, mid, and tail target nucleic acid regions of the polynucleotide to be detected, respectively. The "seed region" of the polynucleotide to be detected refers to a target nucleic acid region composed of about 7-11 nucleotides responsible for a 5' terminal region, the "mid region" to a target nucleic acid region composed of about 7-11 nucleotides responsible for a middle region between the 5' terminus and the 3' terminus, and the "tail region" to a target nucleic acid region composed of about 7-11 nucleotides responsible for a 3' terminal region. The target nucleic acid regions may overlap with each other by about 2-10 consecutive nucleotides.

Conjugated with fluorescents of respective different colors, the three protein-nucleic acid complexes can accurately detect a polynucleotide to be detected through the measurement of fluorescent signals and the multicolor single-molecule fluorescence imaging.

According to an embodiment of the present disclosure, the fluorescent signal measuring method may be carried out by any microscope that can detect a single-molecule fluorescent signal, such as in total internal reflection fluorescence microscopy (TIRF), confocal microscopy, epi-fluorescence microscopy, HiLo microscopy, line-scanning confocal microscopy, etc. For example, the fluorescent signal measuring method may be carried out using TIRF.

As for details of the fluorescent signal measurement, fluorescent signals are measured and then time fractions of bound state between a polynucleotide to be detected and nucleic acid molecules (imagers) having complementary nucleic acid sequences thereto. When the time fractions of bound state measured for all imagers are as high as or higher than a threshold, the polynucleotide is determined to be an on-target polynucleotide. In contrast, when a measurement for even one imager is less than a threshold, the polynucleotide is determined to be an off-target polynucleotide.

The time fraction of bound state may be calculated according to the following Mathematical Formula 1:

$$\text{Time fraction of bound state} = T/P \qquad \text{[Mathematical Formula 1]}$$

T: total time for which a fluorescent signal is sensed

P: detection time

In Mathematical Formula 1, T, total time for which a fluorescent signal is sensed, means a total of times for which a fluorescent signal is sensed. For example, T means a total of times for which a fluorescent signal is sensed by a fluorescence sensing means such as a camera.

The total time (T) for which a fluorescent signal is sensed is a total sum of the times for which a fluorescent signal exclusive of noise is sensed. A person skilled in the art could distinguish between noise and a fluorescent signal. For example, the fluorescent signal distinguished from noise may have a S/N (signal to noise ratio) of 3 or higher.

The total time (T) for which a fluorescent signal is sensed may be a total of times for which a fluorescent signal having a strength (intensity) exceeding that of noise is sensed. The fluorescent signal having a strength (intensity) exceeding that of noise refers to a fluorescent signal having a minimum signal intensity required for identity as a fluorescent signal. A person skilled in the art could detect a fluorescent signal distinguished from noise. In an embodiment, the intensity of noise may be intensity of noise signal that any nucleic acid molecule (imager) having a nucleotide sequence complementary to the target nucleic acid region in a polynucleotide to be detected generates for a polynucleotide intended to be excluded from a polynucleotide to be detected. For example, the intensity of noise may be the maximum value among the intensities that any nucleic acid molecule (imager) having a nucleotide sequence complementary to the target nucleic acid region in a polynucleotide to be detected generates for polynucleotides intended to be excluded from a polynucleotide to be detected, however, a person skilled in the art could detect a fluorescent signal distinguished from noise.

The fluorescent signal higher in intensity than noise may have a signal to ratio (S/N) of more than 1, 1.1 or more, 1.2 or more, 1.3 or more, 1.4 or more, 1.5 or more, 1.6 or more, 1.7 or more, 1.8 or more, 1.9 or more, 2 or more, 2.1 or more, 2.2 or more, 2.3 or more, 2.4 or more, 2.5 or more, 2.6 or more, 2.7 or more, 2.8 or more, 2.9 or more, 3 or more, 3.1 or more, 3.2 or more, 3.3 or more, 3.4 or more, 3.5 or more, 3.6 or more, 3.7 or more, 3.8 or more, 3.9 or more, or 4 or more, for example, 3 or more.

When the time fraction of bound state calculated according to Mathematical Formula 1 is measured to be a threshold or higher for all imagers, the polynucleotide may be determined to be a polynucleotide to be detected. Alternatively, when the time fraction of bound state calculated according to Mathematical Formula 1 is measured to be lower than a threshold for even one imager, the polynucleotide may be determined to be not a polynucleotide to be detected. The threshold may be properly set according to detection purposes. For example, the threshold may have an upper limit as the minimum value among the time fractions of bound state obtained by any nucleic acid molecule (imager) having a nucleic acid sequence complementary to a target nucleic acid region to be detected. Alternatively, the threshold may have a lower limit as the minimum value among the time fractions of bound state obtained by the nucleic acid molecule (imager) for polynucleotides to be excluded as off-targets. In another alternative embodiment, the threshold may be set within a range between the upper limit and the lower limit. For example, the upper limit of the threshold may be set to be the minimum value among the time fractions of bound state obtained by any nucleic acid molecule (imager) having a nucleic acid sequence complementary to a target nucleic acid region to be detected. For one embodiment, the threshold value may be set to be greater than the lower limit to the upper limit or less. For one specific embodiment, the threshold value may be set to be in a range of 0.03 to 0.12, 0.03 to 0.1, 0.03 to 0.07, 0.03 to 0.05, 0.05 to 0.12, 0.05 to 0.1, 0.05 to 0.07, 0.07 to 0.12, 0.07 to 0.1, or 0.1 to 0.12 and may be, for example, one selected from the group consisting of 0.12, 0.1, 0.07, 0.05, and 0.03.

The threshold may be properly set depending on detection purposes. For example, the threshold may be set according to sensitivity and specificity. The threshold may be set to be around the lower limit in order to increase the sensitivity or around the upper limit in order to increase the specificity.

Provided according to another embodiment of the present disclosure is a method for detecting single nucleotide polymorphism (SNP), the method comprising the steps of: contacting the polynucleotide detecting composition with a biological sample containing a polynucleotide to be detected; and measuring a fluorescent signal generated in step (1).

For example, there may be two or more target nucleic acid regions among which two target nucleic acid regions juxtaposed therewith at the 3' and/or the 5' end thereof overlap by 2 to 7 consecutive nucleotides while not overlapping by at least one nucleotide. There may also be two or more nucleic molecules having complementary sequences to the two or more target nucleic acid regions, respectively. In a target nucleic region corresponding to a nucleic acid molecule from which no fluorescent signals are detected, the nucleotide by which a mismatch occurs between the juxtaposed target nucleic acid regions may be determined to be responsible for single nucleotide polymorphism (SNP).

According to an embodiment, two or more polynucleotides to be detected exist in mixture in a biological sample, protein-nucleic acid complexes for detecting corresponding polynucleotides to be detected may be sequentially used for sequential detection of the two or more polynucleotides to be detected. In detail, various different polynucleotides in a biological sample may be immobilized to one detection chip. Two or more polynucleotides, but not one polynucleotide, can be detected per detection chamber. Since the interaction between the protein-nucleic acid complex according to an embodiment of the present disclosure and a target polynucleotide is very dynamic, polynucleotides to be detected can be sequentially detected by only changing a probe (nucleic acid molecule having a nucleotide sequence complementary to a target nucleic acid region of a polynucleotide to be detected) simply through a flow. For instance, with reference to FIG. 2d, Molecule 1 and Molecule 2 are immobilized to one detection chamber and the protein-nucleic acid complex was changed from probe set 1 to probe set 2 at the time point of 1,200 seconds, with the consequent signal shift of molecule 1 and molecule 2 at the same time point. That is, according to an embodiment of the present disclosure, two or more polynucleotide to be detected can be sequentially detected in one detection chamber.

Advantageous Effects

Provided according to the present disclosure is a method for detecting miRNA, using RISC and a fluoro-imaging technique. In detail, the use of the Argonaute protein-probe complex renders miRNA detection up to 10 fold faster than conventional techniques and can detect miRNA mutation at the level of even one nucleotide difference. Furthermore, the method has the advantage of detecting two or more nucleotides simultaneously or sequentially within a short time.

DESCRIPTION OF DRAWINGS

FIG. 1a is a schematic diagram of miRNA tailing processes for immobilizing RNA extracted and isolated from cells to the glass surface of a detection chip as explained in Example 4-1.

FIG. 2*a* shows target miRNAs (let-7a and let-7c) and DNA probe sets targeting the same (probe set 1 for let-7a and probe set 2 for let-7c), as explained in Example 4-3.

FIG. 2*b* shows time fraction measurements of bound states of probe sets 1 and 2 for let-7a and let-7c miRNAs, as explained in Example 4-3.

FIG. 2*c* shows fluorescent signal measurements from the three fluorophorophores (Cy7 for targeting the seed region, Cy3 for targeting the mid region, and Cy5 for targeting the tail region) after Argonaute-loaded probe set 1 is introduced into the detection chip, as explained in Example 5.

FIG. 4*a* shows a design of mismatch target sequences, which each bear a single nucleotide mutation to let-7a, with the corresponding probe DNA comprising a single nucleotide mismatch.

Figure 1B:
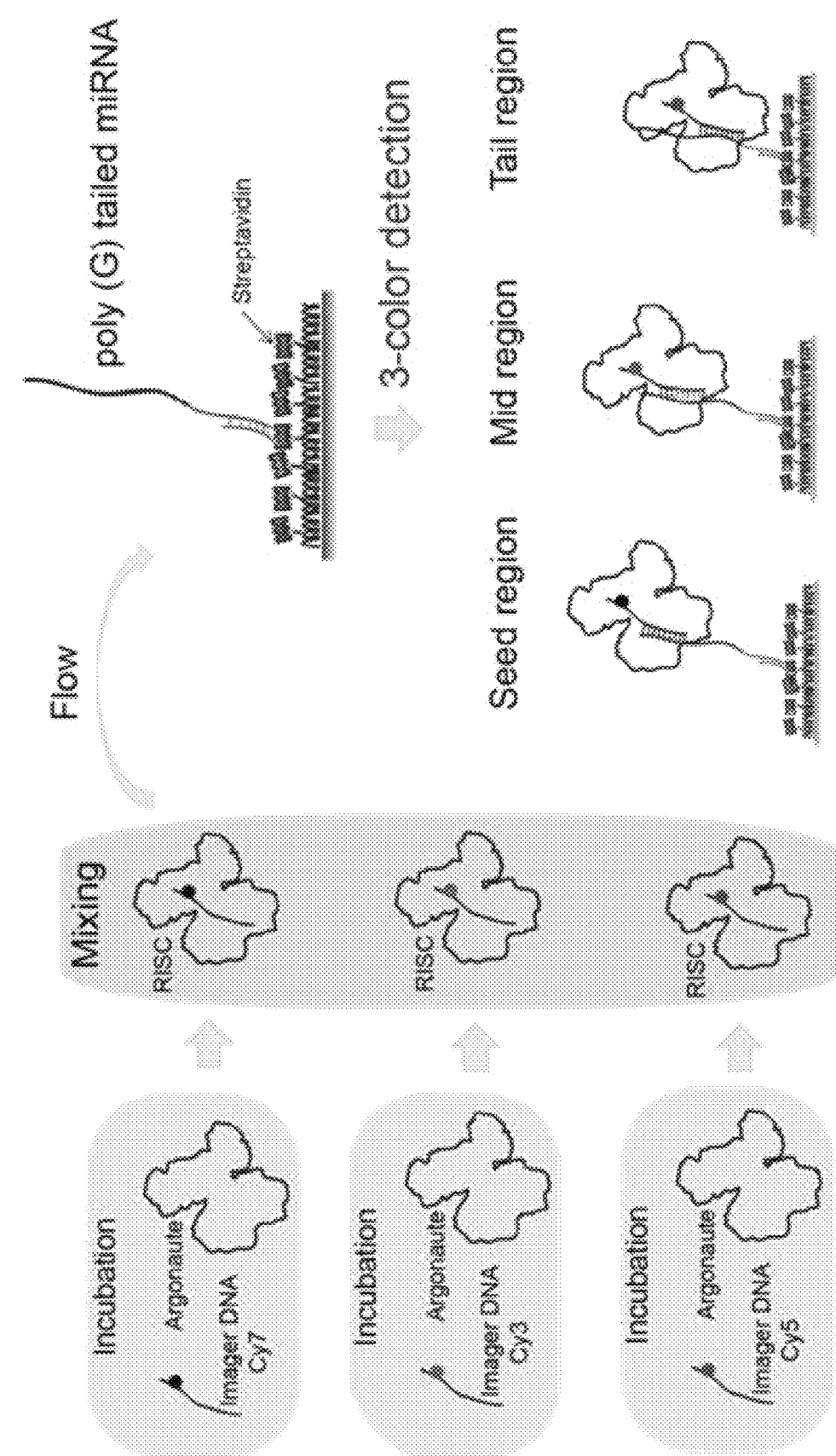
FIG. 1b is a schematic diagram of a miRNA detection method using three different DNA probes binding to seed, mid, and tail regions of a target miRNA, respectively, as explained in Example 4-2, wherein each miRNA is associated with Argonaute protein to form RISC (RNA-induced silencing complex) to promote the binding of the DNA probes to the target RNA.

1 M NaCl, 20 mM Tris-HCl (pH 7.5), and 2 mM $MgCl_2$. The cell lysate was centrifuged at 18,000 rpm for 1 hour and the supernatant was incubated in Ni-NTA agarose resin (Qiagen) at 4° C. for 3 hours. After completion of the incubation, the Ni-NTA resin was washed with a lysis buffer containing 20 mM imidazole, followed by eluting the TtAgo protein with a buffer containing 500 mM NaCl, 20 mM Tris-HCl (pH 7.5), 2 mM $MgCl_2$, and 100 mM imidazole. The N-terminal His-tag was eliminated using TEV protease.

Thereafter, the thermostable TtAgo protein was further purified by thermal treatment at 55° C. for 15 minutes. After the thermal treatment, the TtAgo proteins in the soluble fractions were collected and further purified using a Superdex 200 (GE Healthcare) size exclusion column.

Example 2: DNA Probe Preparation, RNA Isolation, and Poly(G) Tailing 2-1. DNA Probe Preparation Four different oligonucleotides, each having an amine group attached thereto via a chain of 6 carbon atoms, were purchased from Integrated DNA Technology (IDT, Coralville, IA). Sequences of the four oligonucleotides are expressed as SEQ ID NOS: 3 to 6 in Table 1 and named Imagers 1 to 4, respectively. In SEQ ID NOS: 3 to 6, linkers are underlined and T* refers to a thymine residue to which an amine group is attached using the chain of 6 carbon atoms.

TABLE 1

| Name | Nucleotide Sequence (5' > 3') | SEQ ID NO: |
|------|-------------------------------|------------|
| let-7a miRNA | UGA GGU AGU AGG UUG UAU AGU | 1 |
| let-7c miRNA | UGA GGU AGU AGG UUG UAU GGU | 2 |
| Imager1 | Phos-ACT ACC TCA <u>TTT TTT TTT* TTT</u> | 3 |
| Imager2 | Phos-TAC AAC CTA <u>CTC ATT TTT* TTT</u> | 4 |
| Imager3 | Phos-ACT ATA CAA <u>CCA TTA TTT* ATT</u> | 5 |
| Imager4 | Phos-ACC ATA CAA <u>CTT TTA TTT* ATT</u> | 6 |

FIG. 4*c* shows time fractions of bound state of Imager 1, Imager2, Imager3 on target let-7a, mismatch target1, mismatch target2, and mismatch target3.

MODE FOR INVENTION

Hereinafter, the present invention will be described in detail by examples. However, the following examples are only intended to illustrate the invention, but not to limit the scope of the invention.

Example 1: Purification of *Thermus thermophilus* Ago (TtAgo) Protein

A TtAgo protein with His-tag at the N-terminus thereof was constructed. To this end, *Thermus thermophilus* Ago (TtAgo) gene (TT_P0026) was cloned into a pET28a vector (Addgene) which had been modified to contain a TEV protease cleavage site. Subsequently, the recombinant vector was inserted into *Escherichia coli* BL21(DE3) cells which were, in turn, incubated at 18° C. in the presence of 0.5 mM IPTG (isoproply-1-thio-β-D-galactopyranoside) to express the TtAgo gene. Subsequently, TtAgo protein-expressing cells were lysed by sonication in a lysis buffer containing Afterward, the probes Imager1, Imager2, Imager3, and Imager4 were conjugated respectively with Cy3, Cy5, or Cy7 mono NHS-ester, which react with the amine group of each of the linkers. Imager1 (SEQ ID NO: 3) probe was conjugated with Cy7, Imager2 (SEQ ID NO: 4) probe with Cy3, and Imager3 (SEQ ID NO: 5) probe with Cy5 (see FIG. 2*a*).

Next, the fluorolabeled probes were stored in a T50 buffer containing 50 mM NaCl and 10 mM Tris-HCl (pH 8.0).

For use in subsequent experiments, Probe set 1 comprised Imager1, Imager2, and Imager3 and Probe set 2 comprised Imager1, Imager2, and Imager4.

2-2. RNA Isolation and Poly(G) Tailing

From HeLa cells (the Korean Cell Line Bank), miRNA was isolated using TRIzol (Invitrogen) or an mirVana kit (Ambion).

For poly(G) tailing at the 3' terminal of the isolated miRNA, 4 µl of Poly(A) Polymerase Reaction Buffer (100 mM Tris-HCl, pH 7.0, 3.0 mM $MnCl_2$, 0.1 mM EDTA, 1 mM DTT, 500 µg/ml acetylated BSA, 50% glycerol), 0.2 µM RNA, 1 µl of 5 mM GTP, 1 µl of 5 mM ITP, 600 units of yeast Poly(A) polymerase (Thermo Fisher), and RNase-free water are mixed to form 20 µl of a mixture. The isolated RNA and the mixture were incubated at 37° C. for 1 hour. The reaction was terminated by heating 65° C. for 15 minutes.

Example 3: Detection Chip Fabrication and Single-Molecule Experiment 3-1. Detection Chip Fabrication Single-molecule experiments were performed on a total internal reflection fluorescence microscope. First, the glass surface of a quartz slid was coated with a mixture of 40:1 PEG: biotin-PEG to block non-specific bonds between molecules, followed by attachment of a glass coverslip to the quartz slide via a double-sided tape to afford a detection chip.

3-2. Ago-Probe Complex Assembly

Together with 1 μM of the TtAgo prepared in Example 1, 2 μM of each of the dye-conjugated (Cy3, Cy5, or Cy7) probe DNAs prepared in Example 2-1, that is, Imager1, Imager2, Imager3, or Imager4 probe was added to an Ago-DNA assembly buffer containing 100 mM NaCl, 10 mM Tris-HCl (pH 8.0), and 5 mM MgCl$_2$ and incubated at 55° C. for 30 min to assemble Ago-probe complexes (Ago-Imager1, Ago-Imager2, Ago-Imager3, and Ago-Imager4).

3-3. Single-Molecule Experiment

For single-molecule experiments, the poly(G)-tailed miR-NAs prepared in Example 2-2 were incubated with biotinylated a poly (C) DNA strand (30 nt) and immobilized to a chip through streptavidin-biotin interaction.

Next, 3 types of Ago-probe complex different in spectroscopical feature/sequence (Probe set 1 or Probe set 2) prepared in Example 3-2, was 100-fold diluted in an imaging buffer (containing 135 mM KCl, 10 mM Tris-HCl (pH 8.0), 0.5% formamide, 120 mM UREA, 1 mM Mg$^{2+}$, and oxygen scavenging system (4 mg/ml D-(+)-glucose (Sigma-Aldrich), 1 mg/ml glucose oxidase (Sigma-Aldrich), 0.04 mg/ml catalase (Roche), and saturated Trolox 25 mg/50 mL)), and injected together into the detection chip. The experiment was performed at 30° C., and Cy3, Cy5, and Cy7 were excited by 532-nm laser (Compass215M, Coherent, Santa Clara, CA), 640-nm laser (Cube640-100C, Coherent, Santa Clara, CA), and 730-nm laser (PhoxX® 730, Omicron, Germany), respectively. Alternative laser excitation (ALEX), mechanical shutters (LS-3, Uniblitz, Rochester, NY) were employed for substitute to switch the three lasers. Fluorescent signals of Cy3, Cy5, and Cy7 were collected through a water-immersion objective (UPlanSApo 60X, Olympus), separated by using two dichroic mirrors (635dcxr and 740dcxr, Chroma) and one mirror (BB01-E02, Thorlabs), and imaged on an EM-CCD camera (Ixon DV897, Andor). Data were collected by using a home-built program written in Visual C++(Microsoft), and analyzed by using MATLAB (R2010a, The MathWorks) and Origin (8.0, OriginLab).

Example 4. miRNA Sensing Process 4-1. miRNA Tailing for Immobilization to Surface In a first step, poly(G) tail was added to the endogenous RNAs isolated by the method of Example 2-2 (FIG. 1a). The poly (G) tail is used for mobilization onto the surface in the present disclosure. Biotinylated poly (C) DNA strands were attached to the miRNA detection chip through streptavidin-biotin in order to capture miRNAs in a non-selective manner. The biotinylated poly (C) DNA strands were hybridized with the poly (G) RNA tail. A series of the processes is depicted in FIG. 1a.

4-2. miRNA Detection Method Using Three DNA Probes

Detection of a target miRNA was achieved after all of the miRNAs isolated from a sample was immobilized onto a surface in a non-selective manner.

To begin with, three different DNA probes (in Probe set 1 or Probe set 2) were used for targeting seed, mid, and tail regions of a target miRNA (see FIG. 2a).

Since the three DNA probes were distinctly conjugated with fluorescents of three respective different colors, the binding of the probes to miRNAs could be discriminated by total internal reflection fluorescence microscopy (TIRF) using single-molecule multicolor fluorescence imaging. However, when used, such DNA probes are very slow in searching for and binding to miRNA regions complementary thereto so that their targeting miRNAs is not practical.

To solve the problem, DNA probes were loaded to Argonaute protein to accelerate the binding of the DNA probes to miRNAs (see FIG. 1b). FIG. 1b is a schematic diagram of a miRNA detection method using three different DNA probes binding to seed, mid, and tail regions of a target miRNA. The term "seed region" in miRNA refers to a 5'-terminal region about 7-11 nt long, "mid region" to a region about 7-11 nt long between 5' and 3' termini, and "tail region" to a 3'-terminal region about 7-11 nt long. A terminal consecutive nucleotide sequence of the seed region may partially overlap with the mid region and a terminal consecutive nucleotide sequence of the mid region may partially overlap with the tail region.

Since the RNA target regions complementary to the probes of the present disclosure are as short as only 9-11 nt, interaction between miRNAs and the Argonaute-probe complex is very dynamic. Furthermore, when there is a single base mismatch, a remarkably different kinetic parameter is provided, guaranteeing high specificity even at a difference as small as one single nucleotide.

4-3. Validation Test for miRNA Detection Method Using Three DNA Probes

In order to test the miRNA detection method of the present disclosure for validity, two let-7 miRNA families of let-7a and let-7c were employed which are different from each other with respect to only one base in the tail region (FIG. 2a). Nucleotide sequences of let-7a and let-7c miR-NAs are represented by SEQ ID NOS: 1 and 2 in Table 2, respectively. In Table 1, the one nucleotide different compared to let-7a is expressed in bold in SEQ ID NO: 2.

FIG. 2a shows target miRNAs (let-7a and let-7c) and respective DNA probe sets targeting the same. For use in probing let-7a and let-7c, probe set 1 (Imager1, 2, and 3) and probe set 2 (Imager1, 2, and 4) were prepared. The seed region of the target miRNA is probed by Cy7-conjugated Imager1, the mid region by Cy3-conjugated Imager1, and the tail regions of let-7a and let-7c by Cy5-conjugated Imager3 and Imager4, respectively. The seed region refers to a 5'-terminal region about 7-11 nt long, the "mid region" to a region about 7-11 nt long between 5' and 3' termini, and the "tail region" to a 3'-terminal region about 7-11 nt long.

Figure 3A:
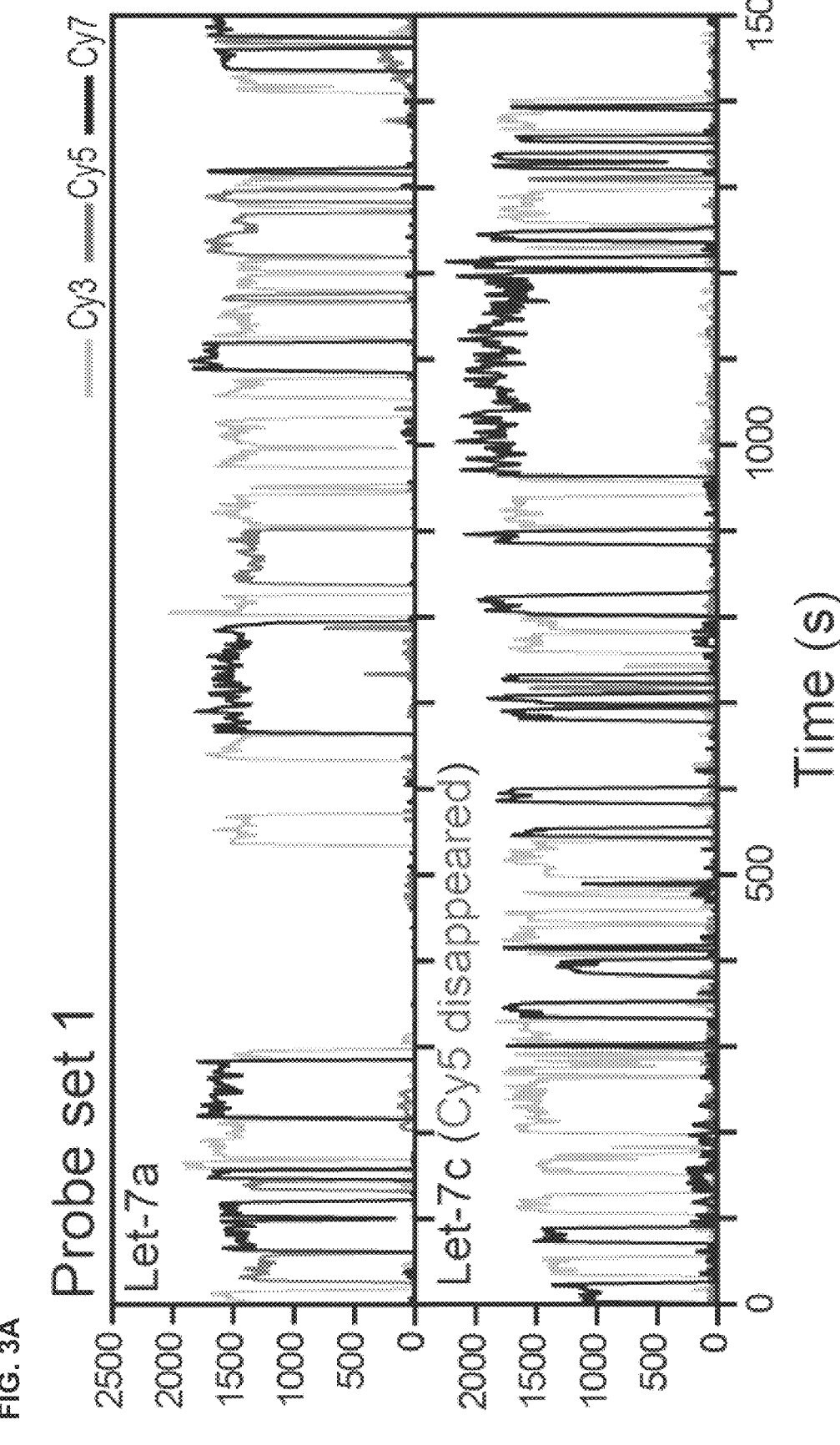
FIG. 3*a* shows representative fluorescence intensive time traces of probe set 1 for let-7a and let7c as explained in Example 4-3.
Figure 3B:
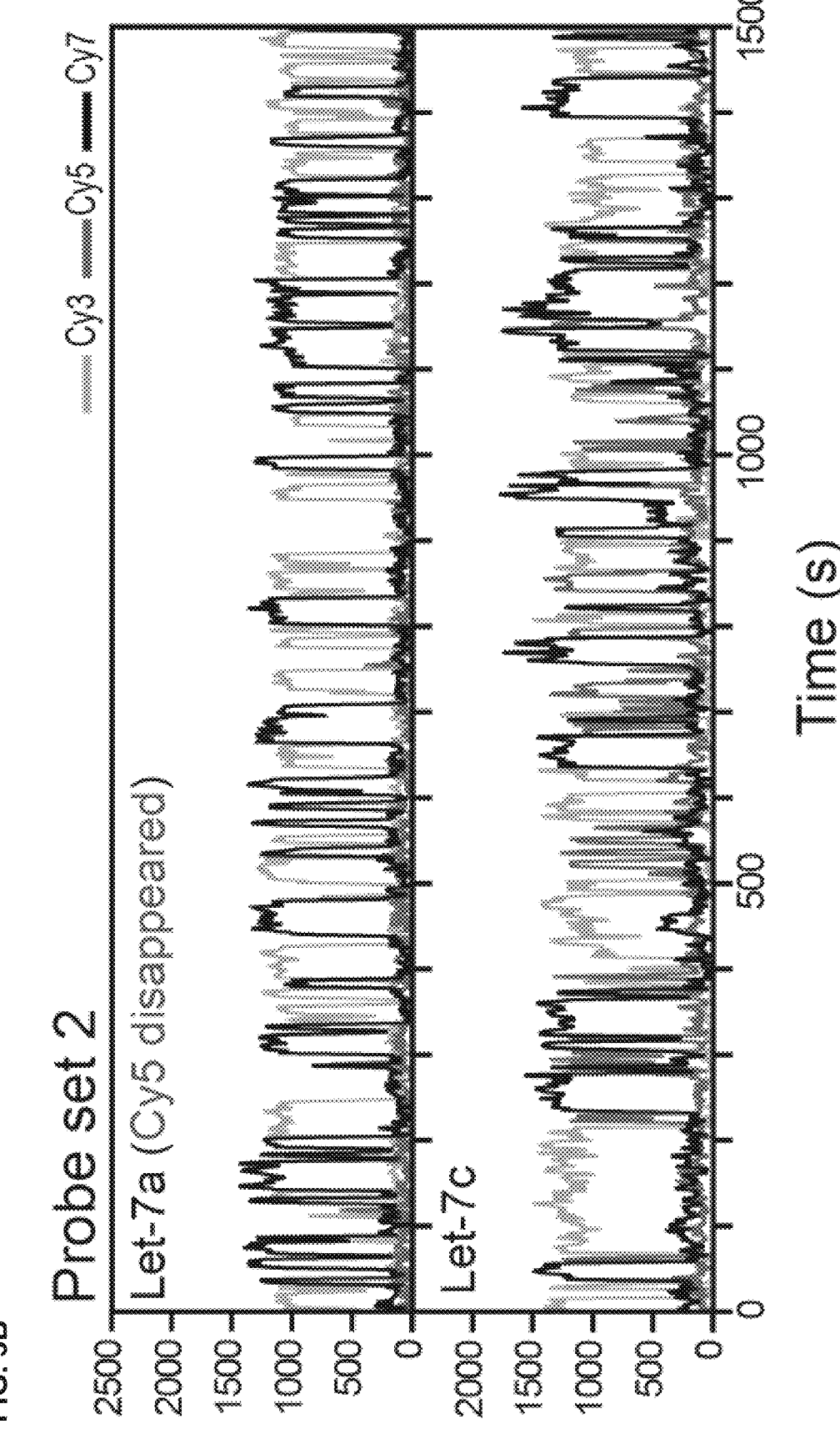
FIG. 3*b* shows representative fluorescence intensity time traces of probe set 2 for let-7a and let7c as explained in Example 4-3.

For single-molecule experiments, the synthetic let-7a and let-7c were immobilized onto the detection chip fabricated in Example 3 and the pre-assembled Argonaute-probe complexes were added thereto. Subsequently, single-molecule detection experiments were performed using the method of Example 3-3, and the results are shown in FIGS. 3a and 3b.

To quantify such kinetic features, the imagers were calculated for time fractions of bound state, and calculation results are depicted in FIG. 2b. FIG. 2b shows time fractions of bound state of probe set 1 and probe set 2 to let-7a and let-7c miRNAs. From the data, it was determined that the time fraction can be used as a standard for sensing let-7a and let-7c.

Taken together, the data demonstrate that the detection method of the present disclosure can explicitly detect miRthree different mismatch target RNAs which were each different in only one nucleotide from the let 7a RNA sequence (SEQ ID NO: 1) were prepared. The three mismatch target RNA sequences thus prepared are given in FIG. 4a and Table 2.

TABLE 2

| Target | Nucleotide Sequence (5'→3') | SEQ ID NO: |
|---|---|---|
| Mismatch target 1 (seed region) | UGA GCU AGU AGG UUG UAU AGU | 7 |
| Mismatch target 2 (mid region) | UGA GGU AGU ACG UUG UAU AGU | 8 |
| Mismatch target 3 (tail region) | UGA GGU AGU AGG UUG UUU AGU | 9 |

NAs (~22 nt) at a single molecule level, and excellent distinguish single bases by using kinetic parameters of the Argonaute-probe complexes.

Example 5. Single-Molecule Detection Experiment of miRNA from Cell Extract

The detection method of the present disclosure was applied to miRNA from a HeLa cell extract. First, endogenous RNA was isolated from HeLa cells, using the method of Example 2-2, and poly (G) tail was added to the isolated RNA. The poly (G)-tailed RNA was hybridized with a biotinylated poly(C) DNA strand and immobilized onto a miRNA detection chip via streptavidin-biotin interaction. Next, the miRNAs isolated from HeLa cells were randomly input into a chamber, followed by Argonaute-loaded probe set 1 and probe set 2. At 30° C., single-molecule fluorescent signals from Cy7 (black), Cy3 (green), and Cy5 (red) were measured using total internal reflection fluorescence microscopy (TIRF), and time fractions were calculated. The results are depicted in FIGS. 2c and 2d.

FIG. 2c shows fluorescent signals measured from the three fluorophorophores (Cy7 for targeting the seed region, Cy3 for targeting the mid region, and Cy5 for targeting the tail region) after Argonaute-loaded probe set 1 is introduced into the detection chip. As shown in FIG. 2c, single-molecule fluorescent signals of Cy7, Cy3, and Cy5 were successfully observed with the introduction of probe set 1, confirming the detection at a single-molecule level.

Figure 2D:
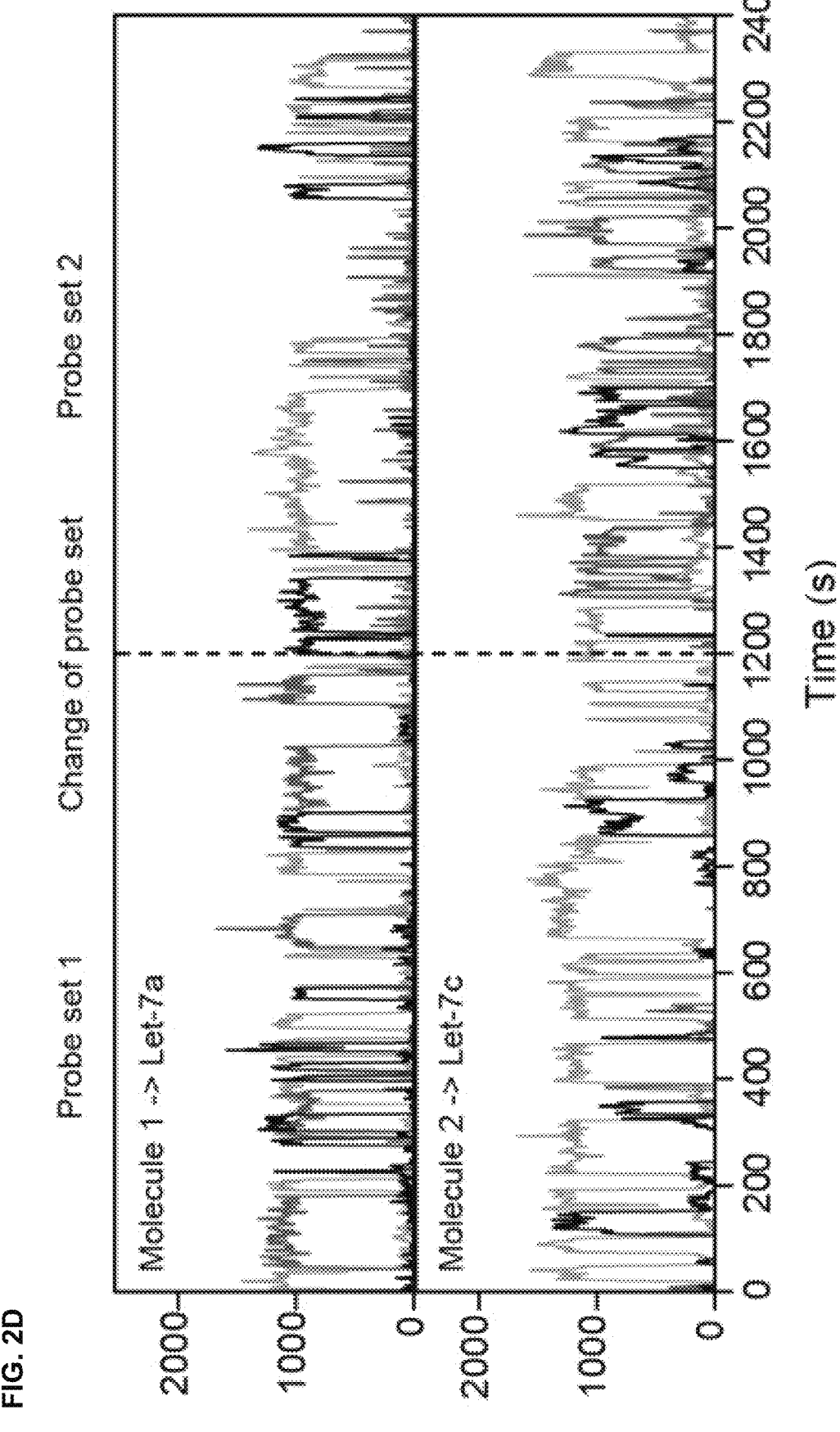
FIG. 2*d* shows representative fluorescence intensity time traces of probe set 1 and probe set 2 for Molecule 1 and Molecule 2, as explained in Example 5.

FIG. 2d depicts representative fluorescence intensity time traces of probe set 1 and probe set 2 for Molecule 1 (upper), and Molecule 2 (lower). Time fractions of bound state for all the imagers of probe set 1 were measured to be 0.1 or higher, and Molecule 1 was classified as let-7a. In contrast, time fractions of bound state for all the imagers of probe set 2 was measured to be 0.1 or higher, and Molecule 2 was classified as let-7c.

Example 6: Identification of Single Nucleotide Polymorphism on miRNA 6-1. Preparation of Three Mismatch Target RNAs The miRNA probing method at a single-molecule level using Argonaute according to the present disclosure was tested for capable of identifying single nucleotide polymorphism (SNP) in addition to probing miRNA. In this regard, As shown in FIG. 4a and Table 2, one nucleotide is mutated in the seed region of let-7a for mismatch target 1, in the mid region for mismatch target 2, and in the tail region for mismatch target 3 (FIG. 4a). Mutated nucleotides are expressed in bold and underlined in Table 2.

6-2. Target Detection Experiment at Single-Molecule Level by Using Mismatch Target Detection experiments were performed on target miRNAs at a single-molecule level in the same manner as in Example 4, using the three mismatch targets prepared in Example 6-1 (Mismatch target 1, Mismatch target 2, and Mismatch target 3) instead of let-7a target sequence. Sequentially, real-time fluorescence traces of Cy3 (green), Cy5 (red), and Cy7 (black) in each of mismatch targets 1-3 were obtained, and representative traces are depicted in FIG. 4b.

Figure 4B:
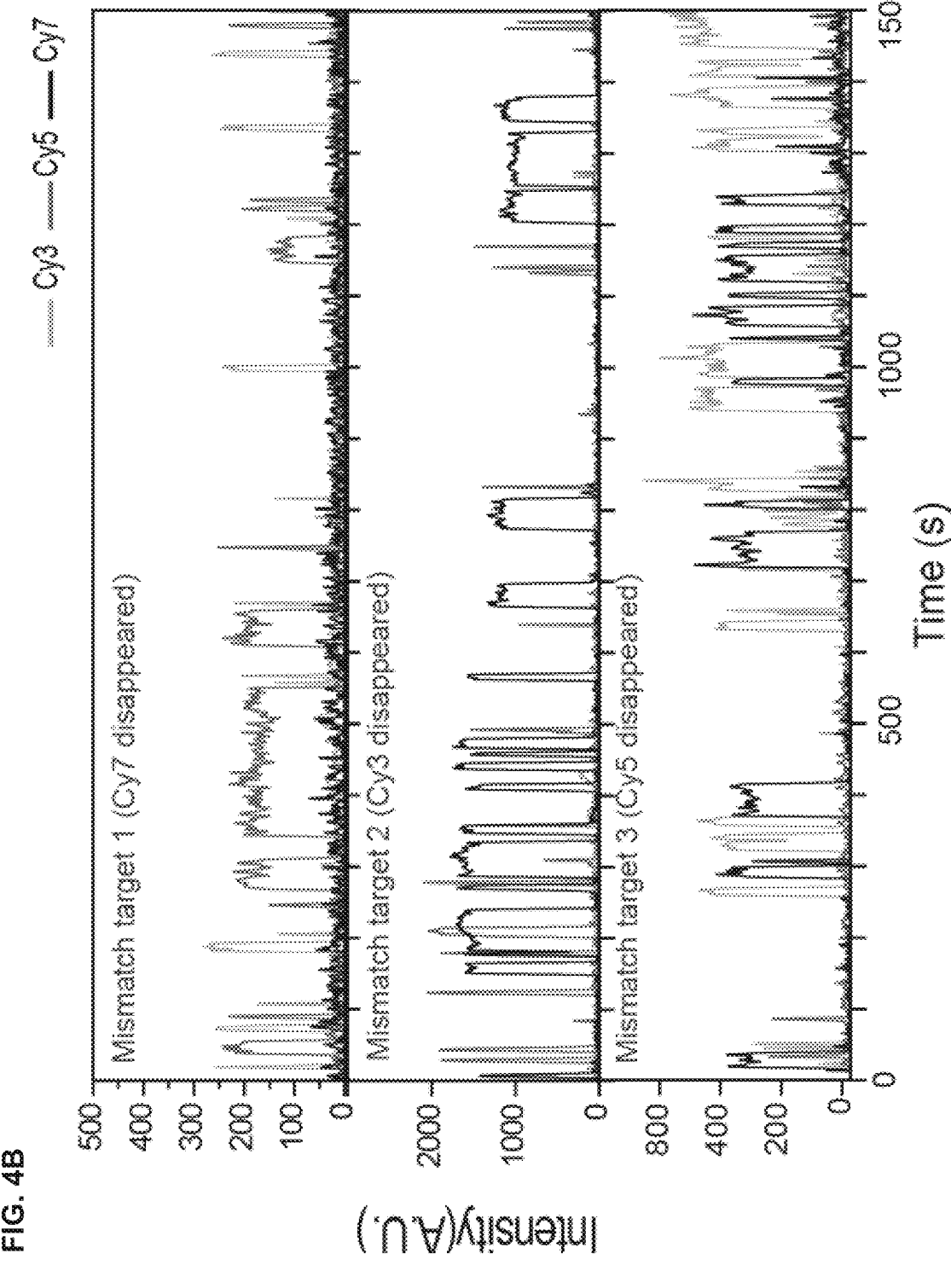
FIG. 4*b* shows representative fluorescence intensity time traces of Cy3 (green), Cy5 (red), and Cy7 (black) in each of mismatch targets 1, 2, and 3, as explained in Example 6-2.

As shown in FIG. 4b, when mismatch targets 1-3 were used, the time fractions of fluorescent signals corresponding to imagers, each containing a noncomplementary base for a mismatch target, significantly decreased. From the result, it is understood that the accurate let-7a sequence can be detected from single nucleotide profiles by excluding mismatches with the aid of kinetic parameters of Ago-Imager DNA complexes.

Next, imager1, imager1, and imager3 in each of let-7a (WT), mismatch target 1, mismatch target 2, and mismatch target 3 were measured for time fraction of bound state (=T/P, T: total time of sensing a fluorescent signal during detection time, P: detection time), and the results are depicted in FIG. 4c. The threshold of time fraction was set to be 0.1.

As shown in FIG. 4c, only the let-7a sequence exhibited time fractions of 0.1 or higher for all the three-type guides. A time fraction less than 0.1 was observed in imager1 for Mismatch target 1, in Imager2 and imager 3 for Mismatch target 2, and in Imager3 for Mismatch target 3.

Therefore, when each of the three fluorescent imagers exhibits a time fraction of 0.1 or higher, the target may be determined as let-7a. When the time fraction is measured to be less than 0.1 for even one of the three fluorescent imagers, the target may be determined to be not let-7a. Thus, exclusion can be made even upon only one base difference. Taken together, the results demonstrate that the measuring method of the present disclosure can identify SNP in addition to detecting RNA at a single base level.

The invention claimed is:

1. A method for detecting a polynucleotide in a biological sample, the method comprising:

(a) contacting a composition for detecting the polynucleotide with the biological sample, wherein the composition for detecting the polynucleotide comprises a first protein-nucleic acid complex comprising an Argonaute protein associated with a first nucleic acid molecule and a second protein-nucleic acid complex comprising an Argonaute protein associated with a second nucleic acid molecule, wherein the first nucleic acid molecule comprises a nucleic acid sequence complementary to a first target nucleic acid region in the polynucleotide to be detected, and the second nucleic acid molecule comprises a nucleic acid sequence complementary to a second target nucleic acid region in the polynucleotide to be detected, wherein the first target nucleic acid region and the second target nucleic acid region differ from each other, and wherein the first nucleic acid molecule is conjugated with a first fluorophore and the second nucleic acid molecule is conjugated with a second fluorophore, wherein the first fluorophore differs from the second fluorophore, wherein the first fluorophore generates a first fluorescent signal, and the second fluorophore generates a second fluorescent signal;

(b) detecting the first and the second fluorescent signals resulting from the contacting of (a), wherein the first fluorescent signal is a fluorescent signal generated by the first fluorophore conjugated with the first nucleic acid sequence bound to the first target nucleic acid region and the second fluorescent signal is a fluorescent signal generated by the second fluorophore conjugated with the second nucleic acid sequence bound to the second target nucleic acid region;

(c) calculating time fractions of bound state for the first fluorescent signal and for the second fluorescent signal according to formula:

Time fraction of bound state = $T/P$, wherein T is a total time of sensing the first or the second fluorescent signal during a detection time, and P is the detection time; and (d) determining that the biological sample comprises the polynucleotide to be detected when the calculated time fraction of bound state for the first fluorescent signal is equal to or higher than a first threshold value set for the first target nucleic acid region and the calculated time fraction of bound state for the second fluorescent signal is equal to or higher than a second threshold value set for the second target nucleic acid region, wherein each of the first and the second threshold values is a value in a range of from 0.03 to 0.12.

2. The method of claim 1, wherein the polynucleotide is selected from the group consisting of DNA, RNA, miRNA, and a combination thereof.

3. The method of claim 1, wherein the biological sample is an isolated cell, a cytolysate, a cell extract, a cell lysate, or an isolated DNA or RNA.

4. The method of claim 1, wherein the biological sample comprises a polynucleotide which has a nucleotide sequence homology of 90% or higher to the polynucleotide to be detected.

5. The method of claim 1, wherein the step of detecting fluorescent signals is carried out using at least one selected from the group consisting of Total Internal Reflection Fluorescence Microscopy (TIRF), confocal microscopy, Epifluorescence microscopy, HiLo microscopy, and Line-scanning confocal microscopy.

6. The method of claim 1, wherein the polynucleotide to be detected has a polynucleotide tail at an end thereof and is immobilized onto a detection chip.

7. A method for detecting a single nucleotide polymorphism (SNP) in a polynucleotide, of the method comprising:

(a) contacting a composition for detecting the polynucleotide with a biological sample comprising the polynucleotide to be detected, wherein the composition for detecting the polynucleotide comprises a first protein-nucleic acid complex comprising an Argonaute protein associated with a first nucleic acid molecule and a second protein-nucleic acid complex comprising an Argonaute protein associated with a second nucleic acid molecule, wherein the first nucleic acid molecule comprises a nucleic acid sequence complementary to a first target nucleic acid region in the polynucleotide to be detected, and the second nucleic acid molecule comprises a nucleic acid sequence complementary to a second target nucleic acid region in the polynucleotide to be detected, wherein the first target nucleic acid region and the second target nucleic acid region differ from each other, and wherein the first nucleic acid molecule is conjugated with a first fluorophore, and the second nucleic acid molecule is conjugated with a second fluorophore, wherein the first fluorophore differs from the second fluorophore, wherein the first fluorophore generates a first fluorescent signal, and the second fluorophore generates a second fluorescent signal;

(b) detecting the first and the second fluorescent signals resulting from the contacting of (a), wherein the first fluorescent signal is a fluorescent signal generated by the first fluorophore conjugated with the first nucleic acid sequence bound to the first target nucleic acid region and the second fluorescent signal is a fluorescent signal generated by the second fluorophore conjugated with the second nucleic acid sequence bound to the second target nucleic acid region;

(c) calculating time fractions of bound state for the first fluorescent signal and for the second fluorescent signal according to formula:

$$\text{Time fraction of bound state} = T/P,$$

wherein T is a total time of sensing the first or the second fluorescent signal during a detection time, and P is the detection time; and (d) determining that the biological sample comprises the polynucleotide to be detected when the calculated time fraction of bound state for the first fluorescent signal is equal to or higher than a first threshold value set for the first target nucleic acid region and the calculated time fraction of bound state for the second fluorescent signal is equal to or higher than a second threshold value set for the second target nucleic acid region, wherein each of the first and the second threshold values is a value in a range of from 0.03 to 0.12.

8. The method of claim 1, wherein the first and/or the second nucleic acid molecule binds to a part of the polynucleotide to be detected.

9. The method of claim 6, wherein the contacting comprises applying the composition to the target polynucleotide to be detected immobilized onto a detection chip.

10. The method of claim 1, wherein the composition for detecting the polynucleotide further comprises a third protein-nucleic acid complex comprising an Argonaute protein associated with a third nucleic acid molecule, wherein the third nucleic acid molecule comprises a nucleic acid sequence complementary to a third target nucleic acid region in the polynucleotide to be detected, wherein the third nucleic acid molecule is conjugated with a third fluorophore different from the first and the second fluorophore and generating a third fluorescent signal, wherein (b) further comprises detecting the third fluorescent signal resulting from the contacting of (a), wherein the third fluorescent signal is a fluorescent signal generated by the third fluorophore conjugated with the third nucleic acid sequence bound to the third target nucleic acid region, wherein (c) further comprises calculating time fraction of bound state for the third fluorescent signal according to formula:

$$\text{Time fraction of bound state} = T/P,$$

wherein T is a total time of sensing the third fluorescent signal during a detection time, and P is the detection time, wherein (d) comprises determining that the biological sample comprises the polynucleotide to be detected when the calculated time fraction of bound state for the first fluorescent signal is equal to or higher than the first threshold value set for the first target nucleic acid region, the calculated time fraction of bound state for the second fluorescent signal is equal to or higher than the second threshold value set for the first target nucleic acid region, and the calculated time fraction of bound state for the third fluorescent signal is equal to or higher than a third threshold value set for the third target nucleic acid region, wherein each of the first, the second, and the third threshold values is a value in a range of from 0.03 to 0.12.

11. The method of claim 7, wherein the composition for detecting the polynucleotide further comprises a third protein-nucleic acid complex comprising an Argonaute protein associated with a third nucleic acid molecule, wherein the third nucleic acid molecule comprises a nucleic acid sequence complementary to a third target nucleic acid region in the polynucleotide to be detected, wherein the third nucleic acid molecule is conjugated with a third fluorophore different from the first and the second fluorophore and generating a third fluorescent signal, wherein (b) further comprises detecting the third fluorescent signal resulting from the contacting of (a), wherein the third fluorescent signal is a fluorescent signal generated by the third fluorophore conjugated with the third nucleic acid sequence bound to the third target nucleic acid region, wherein (c) further comprises calculating time fraction of bound state for the third fluorescent signal according to formula:

$$\text{Time fraction of bound state} = T/P,$$

wherein T is a total time of sensing the third fluorescent signal during a detection time, and P is the detection time, wherein (d) comprises determining that the biological sample comprises the polynucleotide to be detected when the calculated time fraction of bound state for the first fluorescent signal is equal to or higher than the first threshold value set for the first target nucleic acid region, the calculated time fraction of bound state for the second fluorescent signal is equal to or higher than the second threshold value set for the first target nucleic acid region, and the calculated time fraction of bound state for the third fluorescent signal is equal to or higher than a third threshold value set for the third target nucleic acid region, wherein each of the first, the second, and the third threshold values is a value in a range of from 0.03 to 0.12.

12. The method of claim 10, wherein the composition for detecting the polynucleotide further comprises a fourth protein-nucleic acid complex comprising an Argonaute protein associated with a fourth nucleic acid molecule, wherein the fourth nucleic acid molecule comprises a nucleic acid sequence complementary to a fourth target nucleic acid region in the polynucleotide to be detected, wherein the fourth nucleic acid molecule is conjugated with a fourth fluorophore different from the first and the second fluorophore and generating a fourth fluorescent signal, wherein (b) further comprises detecting the fourth fluorescent signal resulting from the contacting of (a), wherein the fourth fluorescent signal is a fluorescent signal generated by the fourth fluorophore conjugated with the fourth nucleic acid sequence bound to the fourth target nucleic acid region, wherein (c) further comprises calculating time fraction of bound state for the fourth fluorescent signal according to formula:

$$\text{Time fraction of bound state} = T/P,$$

wherein T is a total time of sensing the forth fluorescent signal during a detection time, and P is the detection time, wherein (d) comprises determining that the biological sample comprises the polynucleotide to be detected when the calculated time fraction of bound state for the first fluorescent signal is equal to or higher than the first threshold value set for the first target nucleic acid region, the calculated time fraction of bound state for the second fluorescent signal is equal to or higher than the second threshold value set for the first target nucleic acid region, the calculated time fraction of bound state for the third fluorescent signal is equal to or higher than the third threshold value set for the third target nucleic acid region, and the calculated time fraction of bound state for the fourth fluorescent signal is equal to or higher than a fourth threshold value set for the fourth target nucleic acid region, wherein each of the first, the second, the third, and the fourth threshold values is a value in a range of from 0.03 to 0.12.

13. The method of claim 11, wherein the composition for detecting the polynucleotide further comprises a fourth protein-nucleic acid complex comprising an Argonaute protein associated with a fourth nucleic acid molecule, wherein the fourth nucleic acid molecule comprises a nucleic acid sequence complementary to a fourth target nucleic acid region in the polynucleotide to be detected, wherein the fourth nucleic acid molecule is conjugated with a fourth fluorophore different from the first and the second fluorophore and generating a fourth fluorescent signal, wherein (b) further comprises detecting the fourth fluorescent signal resulting from the contacting of (a), wherein the fourth fluorescent signal is a fluorescent signal generated by the fourth fluorophore conjugated with the fourth nucleic acid sequence bound to the fourth target nucleic acid region, wherein (c) further comprises calculating time fraction of bound state for the fourth fluorescent signal according to formula:

$$\text{Time fraction of bound state} = T/P,$$

wherein T is a total time of sensing the fourth fluorescent signal during a detection time, and P is the detection time, wherein (d) comprises determining that the biological sample comprises the polynucleotide to be detected when the calculated time fraction of bound state for the first fluorescent signal is equal to or higher than the first threshold value set for the first target nucleic acid region, the calculated time fraction of bound state for the second fluorescent signal is equal to or higher than the second threshold value set for the first target nucleic acid region, the calculated time fraction of bound state for the third fluorescent signal is equal to or higher than the third threshold value set for the third target nucleic acid region, and the calculated time fraction of bound state for the fourth fluorescent signal is equal to or higher than a fourth threshold value set for the fourth target nucleic acid region, wherein each of the first, the second, the third, and the fourth threshold values is a value in a range of from 0.03 to 0.12.

* * * * *